US010456390B2

(12) United States Patent
Aparici Virgili et al.

(10) Patent No.: US 10,456,390 B2
(45) Date of Patent: *Oct. 29, 2019

(54) COMBINATIONS COMPRISING MABA COMPOUNDS AND CORTICOSTEROIDS

(71) Applicant: ALMIRALL, S.A., Barcelona (ES)

(72) Inventors: Monica Aparici Virgili, Sant Feliu de Llobregat (ES); Marta Calbet Murtro, Sant Feliu de Llobregat (ES); Montserrat Miralpeix Guell, Sant Feliu de Llobregat (ES); Amadeu Gavalda Monedero, Sant Feliu de Llobregat (ES); Carlos Puig Duran, Sant Feliu de Llobregat (ES)

(73) Assignee: Almirall, S.A., Barcelona (ES)

( * ) Notice: Subject to any disclaimer, the term of this patent is extended or adjusted under 35 U.S.C. 154(b) by 0 days.

This patent is subject to a terminal disclaimer.

(21) Appl. No.: 14/906,957

(22) PCT Filed: Jul. 24, 2014

(86) PCT No.: PCT/EP2014/065966
§ 371 (c)(1),
(2) Date: Jan. 22, 2016

(87) PCT Pub. No.: WO2015/011245
PCT Pub. Date: Jan. 29, 2015

(65) Prior Publication Data
US 2016/0175295 A1 Jun. 23, 2016

(30) Foreign Application Priority Data
Jul. 25, 2013 (EP) .................................. 13382305

(51) Int. Cl.
*A61K 31/4709* (2006.01)
*A61K 45/06* (2006.01)
*A61K 31/56* (2006.01)
*A61K 31/573* (2006.01)
*A61K 31/575* (2006.01)
*A61K 31/58* (2006.01)

(52) U.S. Cl.
CPC .......... *A61K 31/4709* (2013.01); *A61K 31/56* (2013.01); *A61K 31/573* (2013.01); *A61K 31/575* (2013.01); *A61K 31/58* (2013.01); *A61K 45/06* (2013.01)

(58) Field of Classification Search
CPC ............ A61K 31/4709; A61K 31/4725; A61K 31/56; A61K 31/573; A61K 31/575; A61K 45/06; C07D 275/06; C07D 409/14; C07D 417/14
See application file for complete search history.

(56) References Cited

U.S. PATENT DOCUMENTS

| 4,556,653 | A | 12/1985 | Giani et al. |
|---|---|---|---|
| 5,397,800 | A | 3/1995 | Alker et al. |
| 6,673,908 | B1 | 1/2004 | Stanton, Jr. |
| 9,072,734 | B2 | 7/2015 | Mitsuyama et al. |
| 9,233,108 | B2 | 1/2016 | Almirall |
| 9,315,463 | B2 | 4/2016 | Prat Quinones et al. |
| 9,579,316 | B2 * | 2/2017 | Julia Jane ............ C07D 409/14 |
| 9,757,383 | B2 | 9/2017 | Almirall |
| 10,005,771 | B2 | 6/2018 | Almirall |
| 2009/0221664 | A1 * | 9/2009 | Ray ...................... A61K 31/401 514/412 |
| 2012/0046467 | A1 | 2/2012 | Mitsuyama et al. |
| 2013/0053359 | A1 | 2/2013 | Prat Quinones et al. |
| 2013/0281415 | A9 | 10/2013 | Prat Quinones et al. |
| 2014/0303127 | A1 | 10/2014 | Bosch et al. |
| 2014/0378421 | A1 | 12/2014 | Bosch et al. |
| 2015/0329535 | A1 | 11/2015 | Sole Feu et al. |
| 2016/0009698 | A1 | 1/2016 | Almirall |
| 2016/0015704 | A1 | 1/2016 | Almirall |
| 2016/0143915 | A1 | 5/2016 | Almirall |
| 2016/0166566 | A1 * | 6/2016 | Julia Jane ............ C07D 409/14 424/131.1 |
| 2016/0200718 | A1 | 7/2016 | Almirall |
| 2016/0264557 | A1 | 9/2016 | Almirall |
| 2017/0275277 | A1 | 9/2017 | Almirall |
| 2018/0015097 | A1 | 1/2018 | Almirall |

FOREIGN PATENT DOCUMENTS

| CN | 101544572 A | 9/2009 |
|---|---|---|
| EP | 0147475 | 10/1985 |
| EP | 1 078 629 | 2/2001 |
| EP | 1 894 568 A1 | 3/2008 |
| EP | 2 386 555 | 11/2011 |

(Continued)

OTHER PUBLICATIONS

T-C Chou et al., Theoretical Basis, Experimental Design and Computerized Simulation of Synergism and Antagonism in Drug Combination Studies, vol. 58 pp. 621-681. Published 2006 (Year: 2006).*

Chung, K.F., "p38 mitogen-activated protein kinase pathways in asthma and COPD," American College of Chest Physicians USA, vol. 139, No. 6, pp. 1470-1479 (2011).

Miller-Larsson, A. et al., "Advances in asthma and COPD treatment: combination therapy with inhaled corticosteroids and long-acting beta 2-agonists," Current Pharmaceutical Design 2006, vol. 12, No. 25, pp. 3261-3279 (2006).

Rogers, D.F., "Tachykinin receptor antagonists for asthma and COPD," Expert Opinion on Therapeutic Patients 2001 GB, vol. 11, No. 7, pp. 1097-1121 (2001).

(Continued)

*Primary Examiner* — Theodore R. West
*Assistant Examiner* — George W Kosturko
(74) *Attorney, Agent, or Firm* — Finnegan, Henderson, Farabow, Garrett & Dunner, LLP

(57) ABSTRACT

A combination which comprises (a) corticosteroid and (b) a dual muscarinic antagonist-β2 adrenergic agonist compound, or any pharmaceutically acceptable salt or solvate thereof.

18 Claims, 2 Drawing Sheets

(56) References Cited

FOREIGN PATENT DOCUMENTS

| | | | | |
|---|---|---|---|---|
| EP | 2 426 121 | | 3/2012 | |
| EP | 2 592 077 | A1 | 5/2013 | |
| EP | 2 592 078 | A1 | 5/2013 | |
| EP | 2592077 | A1 * | 5/2013 | ........... C07D 403/12 |
| EP | 2592077 | A1 * | 5/2013 | ........... C07D 403/12 |
| JP | 2000-515881 | A | 11/2000 | |
| JP | 2010-509391 | A | 3/2010 | |
| JP | 2011-524897 | A | 9/2011 | |
| JP | 2013-519705 | A | 5/2013 | |
| KR | 10-2009-0116053 | A | 11/2009 | |
| WO | WO 1998/04517 | | 2/1998 | |
| WO | WO 98/09632 | | 3/1998 | |
| WO | WO 99/30703 | | 6/1999 | |
| WO | WO-0012067 | A1 * | 3/2000 | ........... C07D 275/06 |
| WO | WO 0012067 | A1 * | 3/2000 | ........... C07D 275/06 |
| WO | WO 01/14339 | | 3/2001 | |
| WO | WO 2004/074246 | | 9/2004 | |
| WO | WO 2004/074276 | | 9/2004 | |
| WO | WO 2004/089892 | | 10/2004 | |
| WO | WO 2004/106333 | | 12/2004 | |
| WO | WO 2005/080375 | | 9/2005 | |
| WO | WO 2005/111004 | | 11/2005 | |
| WO | WO 2005/123693 | A1 | 12/2005 | |
| WO | WO 2006/023454 | | 3/2006 | |
| WO | WO 2006/023457 | | 3/2006 | |
| WO | WO 2006/023460 | | 3/2006 | |
| WO | WO 2007/017670 | | 2/2007 | |
| WO | WO 2007/090859 | | 8/2007 | |
| WO | WO 2007/107828 | | 9/2007 | |
| WO | WO 2008/000483 | | 1/2008 | |
| WO | WO 2008/017824 | | 2/2008 | |
| WO | WO 2008/017827 | | 2/2008 | |
| WO | WO 2008/041095 | | 4/2008 | |
| WO | WO 2008/059245 | | 5/2008 | |
| WO | WO 2008/087437 | A1 | 7/2008 | |
| WO | WO 2008/096127 | | 8/2008 | |
| WO | WO 2008/096129 | | 8/2008 | |
| WO | WO 2008/149110 | | 12/2008 | |
| WO | WO 2009/013244 | | 1/2009 | |
| WO | WO 2009/017813 | | 2/2009 | |
| WO | WO 2009/098448 | | 8/2009 | |
| WO | WO 2009/139709 | | 11/2009 | |
| WO | WO 2009/154562 | A1 | 12/2009 | |
| WO | WO 2010/004517 | | 1/2010 | |
| WO | WO-2010011813 | A1 * | 1/2010 | ........... A61K 9/0073 |
| WO | WO 2010/015792 | | 2/2010 | |
| WO | WO 2010/069504 | A1 | 6/2010 | |
| WO | WO 2010/123766 | | 10/2010 | |
| WO | WO 2011/012897 | | 2/2011 | |
| WO | WO 2011/101374 | A1 | 8/2011 | |
| WO | WO 2011/141180 | | 11/2011 | |
| WO | WO 2012/044825 | | 4/2012 | |
| WO | WO 2012/085582 | | 6/2012 | |
| WO | WO 2012/085583 | | 6/2012 | |
| WO | WO 2012/168349 | | 12/2012 | |
| WO | WO 2012/168359 | | 12/2012 | |
| WO | WO 2013/068552 | | 5/2013 | |
| WO | WO 2013/068554 | | 5/2013 | |
| WO | WO 2013/068875 | | 5/2013 | |
| WO | WO 2013/071009 | A1 | 5/2013 | |
| WO | WO 2013/071169 | A1 | 5/2013 | |
| WO | WO 2014/086924 | | 6/2014 | |
| WO | WO 2014/086927 | | 6/2014 | |
| WO | WO 2014/095920 | | 6/2014 | |
| WO | WO2014095700 | A1 | 6/2014 | |
| WO | WO2014100158 | A1 | 6/2014 | |
| WO | WO 2004/074812 | | 9/2014 | |
| WO | WO 2014/131851 | | 9/2014 | |
| WO | WO 2014/131852 | | 9/2014 | |
| WO | WO 2015/011244 | | 1/2015 | |
| WO | WO 2015/011245 | | 1/2015 | |
| WO | WO2015049574 | A1 | 4/2015 | |
| WO | WO 2016/046390 | | 3/2016 | |

OTHER PUBLICATIONS

Shan, Wen Jun et al., "Dual beta(2)-adrenoceptor agonists-PDE4 inhibitors for the treatment of asthma and COPD," Bioorganic & Medicinal Chemistry Letters, vol. 22, No. 4, pp. 1523-1526 (2012).
Thorsson, L. et al., "Factors guiding the choice of delivery device for inhaled corticosteroids in the long-term management of stable asthma and COPD: Focus on budesonide," Respiratory Medicine, Bailliere Tindall. London, GB, vol. 99, No. 7, pp. 836-849 (2005).
International Search Report for International Patent Application No. PCT/EP2014/065966, dated Aug. 19, 2014.
U.S. Appl. No. 13/697,060, filed Nov. 9, 2012.
U.S. Appl. No. 14/357,344, filed May 9, 2014.
U.S. Appl. No. 14/357,400, filed May 9, 2014.
U.S. Appl. No. 14/653,048, filed Jun. 17, 2015.
U.S. Appl. No. 14/770,200, filed Aug. 27, 2015.
U.S. Appl. No. 14/770,206, filed Aug. 27, 2015.
U.S. Appl. No. 14/956,767, filed Dec. 2, 2015.
U.S. Appl. No. 14/956,836, filed Dec. 2, 2015.
U.S. Appl. No. 14/906,991, filed Jan. 22, 2016.
International Search Report, PCT/EP2012/072309, dated Dec. 18, 2012.
International Search Report PCT/EP2012/072311, dated Dec. 10, 2012.
International Search Report PCT/EP2011/002376, dated Aug. 1, 2011.
International Search Report PCT/EP2013/076973, dated Mar. 11, 2014.
International Search Report PCT/EP2014/053874, dated Apr. 17, 2014.
International Search Report PCT/EP2014/053871, dated Mar. 27, 2014.
International Search Report PCT/EP2014/065965, dated Sep. 18, 2014.
Barnes, Peter J., "Airway Pharmacology," Textbook of Respiratory Medicine, 3rd Edition, Chapter 11, 2000, pp. 267-272.
Glossop, Paul A. et al., "Progress in the Development of Inhaled, Long-Acting β2-Adrenoceptor Agonists," Annual Reports in Medicinal Chemistry, vol. 41, 2006, pp. 237-248.
Hoffman, Brian B. "Catecholamines, Sympathomimetic Drugs, and Adrenergic Receptor Antagonists," Goodman & Gilman's The Pharmacological Basis of Therapeutics 10th Edition, Chapter 10, pp. 215-232, 2001.
Hughes, Adam et al., Dual-pharmacology Muscarinic Antagonist and β2 Agonist Molecules for the Treatment of Chronic Obstructive Pulmonary Disease, Future Med. Chem., (2011), 3(13), pp. 1585-1605.
Jacobsen, John R., "Third-generation Long-Acting β2 Adrenoceptor Agonists: Medicinal Chemistry Strategies Employed in the Identification of Once-Daily Inhaled β2-Adrenoceptor Agonists," Future Med Chem., 2011, 3(13). pp. 1607-1622.
Naito, Roy et al., "Synthesis and Antimuscarinic Properties of Quinuclidin-3-yl 1,2,3,4-Tetrahydroisoquinoline-2-carboxylate Derivatives as Novel Muscarinic Receptor Antagonists," J. Med Chem., 2005, 48, pp. 6597-6606.
Van Noord, J.A., "Comparison of tiotropium once Daily, Formoterol Twice Daily and Both Combined Once Daily in Patients with COPD," European Respiratory Journal, vol. 26, No. 2., pp. 214-222, 2005.
Bateman, E.D., "Pharmacodynamics of GSK961081, a bi-functional molecule, In patients with COPD," Pulmonary Pharmacology & Therapeutics, vol. 26, pp. 581-587 (2013).
Hughes, A.D. et al., "Multivalent Dual Pharmacology Muscarinic Antagonist and β2 Agonist (MABA) Molecules for the Treatment of COPD, Progress in Medicinal Chemistry," vol. 51, pp. 71-95 (2012).
Hughes, A.D. "Discovery of Muscarinic Acetylcholine Receptor Antagonist and Beta-2 Adrenoceptor Agonist (MABA) Dual Pharmacology Molecules," Respiratory Drug Delivery Europe, pp. 47-58 (2013).
McNamara, A., et al., Preclinical Efficacy of THRX-200495, a Dual Pharmacology Muscarinic Receptor Antagonist and β2-Adrenocep-

(56) References Cited

OTHER PUBLICATIONS tor Agonist (MABA), Pulmonary Pharmacology & Therapeutics, xxx pp. 1-7 (2012). Article in press.
Norman, P., "Evalutation of WO-2012085582 and WO-2012085583 two identified MABAs: backups to AZD-2115?" Expert Opin. Ther. Patents, 22(11), pp. 1377-1383 (2012).
Norman, P., "Novel dihydroquinoline-based MABAs; clues to the identity of LAS-190792: evaluation of WO20111411802," Expert Opin. Ther. Patents, 22:2, pp. 185-192 (2012).
Norris, V. et al., "Bronchodilation and Safety of Supratherapeutic Doses of Salbutamol or Ipratropium Bromide Added to Single Dose GSK961081 in Patients with Moderate to Severe COPD," Pulmonary Pharmacology and Therapeutics, vol. 26, pp. 574-580 (2013).
Welders, Pascal L.M.L. et. al., "A New Class of Bronchodilator Improves Lung Function in COPD: a trial with GSK961081" Eur Respir J. 42: pp. 972-981 (2013).
Banerjee, R., et al., "Synthon Robustness in Saccharinate Salts of Some Substituted Pyridines," CrystEngComm, 8: pp. 680-685 (2006).
Bastin, R.J., et. al., "Salt Selection and Optimisation Procedures for Pharmaceutical New Chemical Entities," Org. Process Res Dev, 4, pp. 427-435 (2000).
Ray, Nicholas C. et al., "Muscarinic antagonist-β-adrenergic agonist dual pharmacology molecules as bronchodilators: a patent review," Informa Healthcare, vol. 19, No. 1, pp. 1-12 (2009).
Restriction Requirement dated Feb. 20, 2015, in U.S. Appl. No. 13/697,060.
Restriction Requirement dated Feb. 18, 2015, in U.S. Appl. No. 14/357,400.
Office Action dated Feb. 3, 2015, U.S. Appl. No. 14/357,344.
Office Action dated Jun. 2, 2015, U.S. Appl. No. 14/357,344.
Notice of Allowance dated Sep. 2, 2015, in U.S. Appl. No. 14/357,344.
U.S. Appl. No. 15/068,926, filed Mar. 14, 2016.
Requirement for Restriction/Election dated Feb. 11, 2016, for U.S. Appl. No. 14/770,200.
Requirement for Restriction/Election dated Mar. 21, 2016, for U.S. Appl. No. 14/956,767.
Notice of Allowance dated Dec. 15, 2015, in U.S. Appl. No. 13/697,060.
Notice of Allowance dated Aug. 3, 2016, in U.S. Appl. No. 14/653,048.
Notice of Allowance dated Sep. 13, 2016, in U.S. Appl. No. 14/956,836.
Notice of Allowance dated Sep. 26, 2016, in U.S. Appl. No. 14/770,206.
Non-Final Office Action dated Aug. 4, 2015, for U.S. Appl. No. 13/697,060.
Non-Final Office Action dated Mar. 8, 2016, for U.S. Appl. No. 14/956,836.
Non-Final Office Action dated Mar. 21, 2016, for U.S. Appl. No. 14/653,048.
Non-Final Office Action dated May 5, 2016, for U.S. Appl. No. 14/770,206.
Non-Final Office Action dated Jun. 10, 2016, for U.S. Appl. No. 14/770,200.
Non-Final Office Action dated Jul. 8, 2016, for U.S. Appl. No. 14/956,767.
Non-Final Office Action dated Jul. 11, 2016 in U.S. Appl. No. 15/068,926.
Non-Final Office Action dated Aug. 11, 2016, for U.S. Appl. No. 14/906,991.
Berge, S. et al., Pharmaceut. Sc., 1977, vol. 66(1), pp. 1-19.
Final Office Action dated Nov. 30, 2016, for U.S. Appl. No. 14/770,200.
Final Office Action dated Dec. 1, 2016, for U.S. Appl. No. 14/956,767.
P. Heinrich Stahl, Camille G. Wermuth. Handbook of Pharmaceutical Salts. Properties, Selection, and Use. Chapter 12, "Monographs on Acids and Bases", pp. 264-267, 283, 284, 290-293 and 300; Chapter 7, "A procedure for Salt Selection and Optimization", pp. 162-177 and 183-188; Chapter 2, "Solubility and Dissolution of Weak Acids, Bases and Salts"; pp. 19 and 28; Wiley-VCH; 2002.
International Search Report of International Application No. PCT/EP2015/072158, dated Nov. 2, 2015.
Written Opinion of the International Searching Authority for International Application No. PCT/EP2015/072158.
U.S. Appl. No. 15/514,294, filed Mar. 24, 2017.
U.S. Appl. No. 15/668,817, filed Aug. 4, 2017.
Nocker R. E. et al., "Interleukin-8 in airway inflammation in patients with asthma and chronic obstructive pulmonary disease," International Archives of Allergy and Immunology, 1996, 109 (2): 183-91.
Milara J et al., "Neutrophil Activation in Severe, Early-Onset COPD Patients versus Healthy Non-Smoker Subjects in vitro: Effects of Antioxidant Therapy," Respiration 2012; 83, 147-158.
Yamamoto C. et al., "Airway inflammation in COPD assessed by sputum levels of interleukin-8*," Chest, 1997, 112 (2): 505-10.
Brittain, Harry G., "Theory and Principles of Polymorphic Systems," Polymorphism in Pharmaceutical Solids, Second Addition, Drugs and the Pharmaceutical Sciences, vol. 192, pp. 1-4, 15-19, 318-430 (2009).
Banerjee, Rahul et al., "Saccharin Salts of Active Pharmaceutical Ingredients, Their Crystal Structures, and Increase water Solubilities," Crystal Growth and Design, vol. 5, No. 6, pp. 2299-2309 (2005).
Hughes, Adam D. et al., "Discovery of muscarinic acetylcholine receptor antagonist and beta 2 adrenoceptor agonist (MABA) dual pharmacology molecules," Bioorganic & Medicinal Chemistry Letters 21, pp. 1354-1358 (2011).
Paulekuhn, G. S. et al., "Trends in Active Pharmaceutical Ingredient Salt Selection based on Analysis of the Orange Book Database," J. Med. Chem, vol. 50, pp. 6665-6672 (2007).
Office Action dated Apr. 27, 2018 in U.S. Appl. No. 15/668,817.
Restriction Requirement dated Oct. 20, 2017, in U.S. Appl. No. 15/668,817.

\* cited by examiner

Fig. 1 Effects of Cpd 2 and its combination with mometasone in inhibiting IL-8 secretion induced by LPS in peripheral blood neutrophils from healthy subjects.
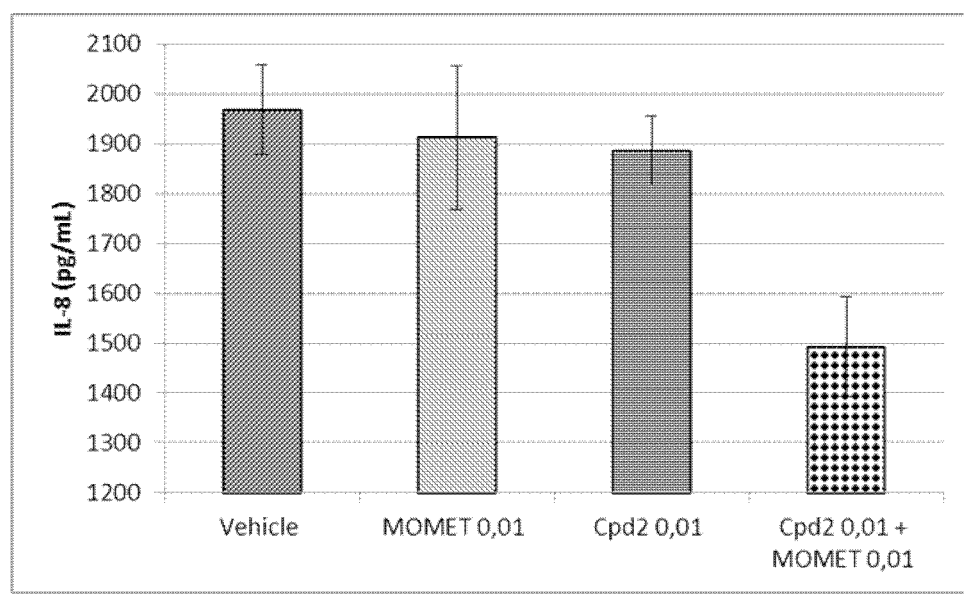

Fig. 2 Effects of Cpd 2 and its combination with fluticasone in inhibiting IL-8 secretion induced by LPS in peripheral blood neutrophils from healthy subjects.
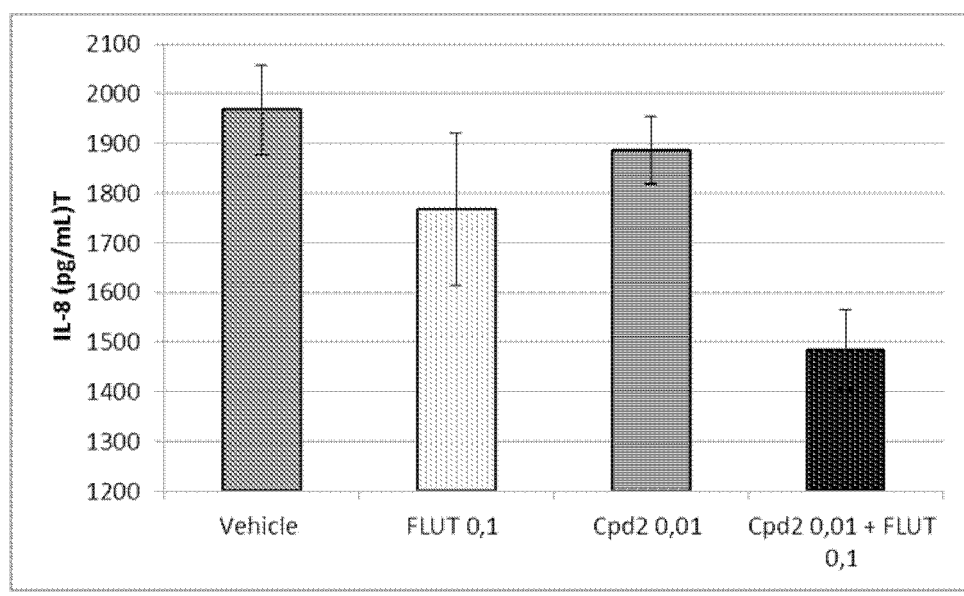

COMBINATIONS COMPRISING MABA COMPOUNDS AND CORTICOSTEROIDS

This application is a national stage filing under 35 U.S.C. § 371 of International Application No. PCT/EP2014/065966, filed on Jul. 24, 2014, which claims priority of European Patent Application No. 13382305.4, filed on Jul. 25, 2013. The contents of these applications are each incorporated herein by reference.

The present invention relates to a combination of two or more pharmaceutically active substances for use in the treatment of respiratory diseases. In particular, the present invention relates to a combination of a corticosteroid with a compound having a dual muscarinic antagonist and a β2 adrenergic agonist activity (MABA).

BACKGROUND OF THE INVENTION

Trans-4-[{3-[5-({[(2R)-2-hydroxy-2-(8-hydroxy-2-oxo-1,2-dihydroquinolin-5-yl)ethyl]amino}methyl)-1H-1,2,3-benzotriazol-1-yl]propyl}(methyl)amino]cyclohexyl hydroxy(di-2-thienyl)acetate is described in WO 2013/068552 and WO 2013/068554. It has the structure shown below.

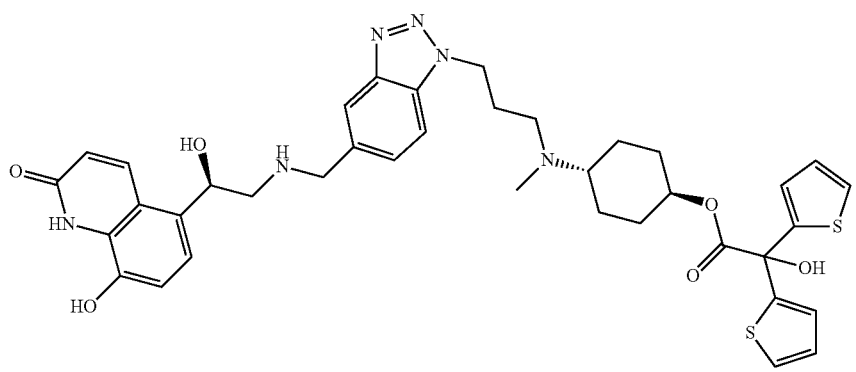

(I)

The compound of formula (I) is a potent dual-acting muscarinic antagonist-β2 agonist (MABA) intended for administration by inhalation for treatment of respiratory diseases, especially asthma and chronic obstructive pulmonary disease (COPD), currently in clinical trials.

DESCRIPTION OF THE INVENTION

Surprisingly, an unexpectedly beneficial therapeutic effect can be observed in the treatment of inflammatory or obstructive diseases of the respiratory tract if a dual muscarinic antagonist-β2 adrenergic agonist compound of the present invention is used with one or more corticosteroids.

In particular, the combination of a dual muscarinic antagonist-β2 adrenergic agonist compound of the present invention with a corticosteroid produces significantly greater inhibition of Interleukin-8 (IL-8) secretion, which is associated with inflammatory and obstructive diseases of the respiratory tract, as compared to that obtained with the corticosteroid alone.

Thus, the present invention provides a combination which comprises (a) a corticosteroid and (b) a dual muscarinic antagonist-β2 adrenergic agonist compound which is Trans-4-[{3-[5-({[(2R)-2-hydroxy-2-(8-hydroxy-2-oxo-1,2-dihydroquinolin-5-yl)ethyl]amino}methyl)-1H-1,2,3-benzotriazol-1-yl]propyl}(methyl)amino]cyclohexyl hydroxy(di-2-thienyl)acetate, or any pharmaceutically acceptable salt or solvate thereof.

The invention also provides a pharmaceutical composition comprising the combination of the present invention and a pharmaceutically-acceptable carrier.

The invention also provides a method of treating a disease or condition associated with dual muscarinic receptor and β2 adrenergic receptor activities (e.g. a pulmonary disease, such as asthma or chronic obstructive pulmonary disease, pre-term labor, glaucoma, a neurological disorder, a cardiac disorder, inflammation, urological disorders such as urinary incontinence and gastrointestinal disorders such as irritable bowel syndrome or spastic colitis) in a mammal, comprising administering to the mammal, a therapeutically effective amount of a compound of formula (I) with a corticosteroid.

Also is provided a product, a kit of parts or a package comprising (a) a corticosteroid and (b) a dual muscarinic antagonist-β2 adrenergic agonist compound of formula (I), as a combined preparation for simultaneous, concurrent, separate or sequential use in the treatment of a patient suffering from or susceptible to a disease as defined above.

DETAILED DESCRIPTION OF THE INVENTION

The term "therapeutically effective amount" refers to an amount sufficient to effect treatment when administered to a patient in need of treatment.

The term "treatment" as used herein refers to the treatment of a disease or medical condition in a human patient which includes:

(a) preventing the disease or medical condition from occurring, i.e., prophylactic treatment of a patient;

(b) ameliorating the disease or medical condition, i.e., causing regression of the disease or medical condition in a patient;

(c) suppressing the disease or medical condition, i.e., slowing the development of the disease or medical condition in a patient; or (d) alleviating the symptoms of the disease or medical condition in a patient.

The phrase "disease or condition associated with muscarinic receptor and β2 adrenergic receptor activities" includes all disease states and/or conditions that are acknowledged now, or that are found in the future, to be associated with both muscarinic receptor and β2 adrenergic receptor activity.

Such disease states include, but are not limited to, pulmonary diseases, such as asthma and chronic obstructive pulmonary disease (including chronic bronchitis and emphysema), as well as neurological disorders and cardiac disorders. β2 adrenergic receptor activity is also known to be associated with pre-term labor (see International Patent Application Publication Number WO 98/09632), glaucoma and some types of inflammation (see International Patent Application Publication Number WO 99/30703 and Patent Application Publication Number EP 1 078 629).

On the other hand M3 receptor activity is associated with gastrointestinal-tract disorders such as Irritable bowel syndrome (IBS) (see, for ex., U.S. Pat. No. 5,397,800), gastrointestinal (GI) ulcers, spastic colitis (see, for ex., U.S. Pat. No. 4,556,653); urinary-tract disorders such as urinary incontinence (see, for ex., J. Med. Chem., 2005, 48, 6597-6606), pollakiuria; motion sickness and vagally induced sinus bradycardia.

The compounds of the invention may exist in both unsolvated and solvated forms. The term solvate is used herein to describe a molecular complex comprising a compound of the invention and an amount of one or more pharmaceutically acceptable solvent molecules. The term hydrate is employed when said solvent is water. Examples of solvate forms include, but are not limited to, compounds of the invention in association with water, acetone, dichloromethane, 2-propanol, ethanol, methanol, dimethylsulfoxide (DMSO), ethyl acetate, acetic acid, ethanolamine, or mixtures thereof. It is specifically contemplated that in the present invention one solvent molecule can be associated with one molecule of the compounds of the present invention, such as a hydrate.

Furthermore, it is specifically contemplated that in the present invention, more than one solvent molecule may be associated with one molecule of the compounds of the present invention, such as a dihydrate. Additionally, it is specifically contemplated that in the present invention less than one solvent molecule may be associated with one molecule of the compounds of the present invention, such as a hemihydrate.

Furthermore, solvates of the present invention are contemplated as solvates of compounds of the present invention that retain the biological effectiveness of the non-solvate form of the compounds.

The respiratory disease or condition to be treated with the formulations and methods of the present invention is typically asthma, acute or chronic bronchitis, emphysema, chronic obstructive pulmonary disease (COPD), bronchial hyperreactivity or rhinitis, in particular asthma or chronic obstructive pulmonary disease (COPD).

The term "pharmaceutically-acceptable salt" refers to a salt prepared from a base or acid which is acceptable for administration to a patient, such as a mammal. Such salts can be derived from pharmaceutically-acceptable inorganic or organic bases and from pharmaceutically-acceptable inorganic or organic acids.

Salts derived from pharmaceutically-acceptable acids include acetic, benzenesulfonic, benzoic, camphorsulfonic, citric, ethanesulfonic, formic, fumaric, gluconic, glutamic, hydrobromic, hydrochloric, hydrofluoric, lactic, maleic, malic, mandelic, methanesulfonic, mucic, nitric, pantothenic, phosphoric, succinic, sulfuric, tartaric, p-toluenesulfonic, xinafoic (1-hydroxy-2-naphthoic acid), napadisilic (1,5-naphthalenedisulfonic acid), triphenyl acetic and the like.

Salts derived from pharmaceutically-acceptable inorganic bases include aluminum, ammonium, calcium, copper, ferric, ferrous, lithium, magnesium, manganic, manganous, potassium, sodium, zinc and the like.

Salts derived from pharmaceutically-acceptable organic bases includes sulfimide derivatives, such as, benzoic sulfimide (also known as saccharin), thieno[2,3-d]isothiazol-3(2H)-one 1,1-dioxide and isothiazol-3(2H)-one 1,1-dioxide, salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

Typically, the compound of formula (I), in the combination product of the present invention, is administered in the form a salt derived from pharmaceutically-acceptable sulfimide derivative, such as, benzoic sulfimide (also known as saccharin), thieno[2,3-d]isothiazol-3(2H)-one 1,1-dioxide and isothiazol-3(2H)-one 1,1-dioxide or from pharmaceutically acceptable acids including citric, lactic, mucic, L-tartaric acid, pantothenic, glucuronic, lactobionic, gluconic, 1-hydroxy-2-naphthoic, mandelic, malic, methanesulfonic, ethanedisulfonic, benzenesulphonic, p-toluenesulfonic, naphthalene-1,5-disulfonic, napthalene-2-sulfonic, (1S)-camphor-10-sulfonic. Particularly preferred are salts derived from benzoic sulfimide (saccharin).

Salts derived from saccharin (benzoic sulfimide) are typically saccharinate or disaccharinate and pharmaceutically acceptable solvates thereof. The MABA compound trans-4-[{3-[5-({[(2R)-2-hydroxy-2-(8-hydroxy-2-oxo-1,2-dihydroquinolin-5-yl)ethyl]amino}methyl)-1H-1,2,3-benzotriazol-1-yl]propyl}(methyl)amino]cyclohexyl hydroxy(di-2-thienyl)acetate is preferably administered in the form of a saccharinate salt (ie. trans-4-[{3-[5-({[(2R)-2-hydroxy-2-(8-hydroxy-2-oxo-1,2-dihydroquinolin-5-yl)ethyl] amino}methyl)-1H-1,2,3-benzotriazol-1-yl]propyl} (methyl)amino]cyclohexyl hydroxy(di-2-thienyl)acetate, saccharinate) having the following chemical structure:

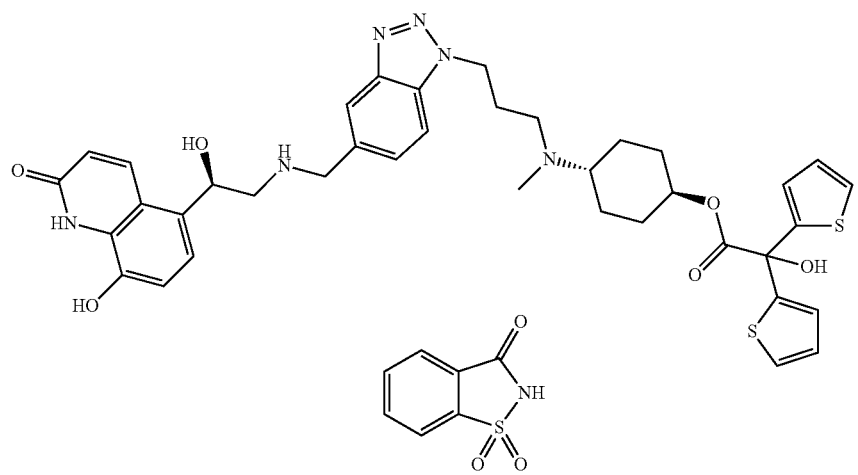 [SMILES: CN(CCCn1nnc2cc(CNC[C@H](O)c3ccc(O)c4[nH]c(=O)ccc34)ccc21)[C@H]1CC[C@H](OC(=O)C(O)(c2cccs2)c2cccs2)CC1 ; O=C1NS(=O)(=O)c2ccccc21]

Typically the combination contains the active ingredients (a) and (b) forming part of a single pharmaceutical composition.

Also provided is a product comprising (a) a corticosteroid and (b) a dual muscarinic antagonist-β2 adrenergic agonist of the invention as a combined preparation for simultaneous, separate or sequential use in the treatment of a human or animal patient.

Typically the product is for simultaneous, separate or sequential use in the treatment of a respiratory disease which is asthma, acute or chronic bronchitis, emphysema, chronic obstructive pulmonary disease (COPD), bronchial hyperreactivity or rhinitis in a human or animal patient.

The present invention further provides the use of (a) a corticosteroid and (b) a dual muscarinic antagonist-β2 adrenergic agonist of the invention for the preparation of a medicament for simultaneous, concurrent, separate or sequential use in the treatment of a said respiratory disease in a human or animal patient.

Also provided is the use of (b) a dual muscarinic antagonist-β2 adrenergic agonist of the invention for the preparation of a medicament, for simultaneous, concurrent, separate or sequential use in combination with (a) a corticosteroid for the treatment of a said respiratory disease in a human or animal patient.

Also provided is the use of (a) a corticosteroid for the preparation of a medicament for use in the treatment of a said respiratory disease in a human or animal patient by simultaneous, concurrent, separate or sequential co-administration in combination with (b) a dual muscarinic antagonist-β2 adrenergic agonist of the invention.

The invention further provides a dual muscarinic antagonist-β2 adrenergic agonist compound of the invention for simultaneous, concurrent, separate or sequential use in combination with a corticosteroid for the treatment of a said respiratory disease.

The invention further provides (a) a corticosteroid as for simultaneous, concurrent, separate or sequential use in combination with (b) a dual muscarinic antagonist-β2 adrenergic agonist compound of the invention for the treatment of a said respiratory disease.

The invention further provides a combination of the invention for simultaneous, concurrent, separate or sequential use in the treatment of a said respiratory disease.

Typically said respiratory disease is selected from asthma, acute or chronic bronchitis, emphysema, chronic obstructive pulmonary disease (COPD), bronchial hyperreactivity and rhinitis, preferably selected from asthma and chronic obstructive pulmonary disease (COPD).

Preferably said patient is human.

Also provided is a pharmaceutical composition comprising (a) a corticosteroid and (b) a dual muscarinic antagonist-β2 adrenergic agonist of the invention in association with (c) a pharmaceutically acceptable carrier or diluent.

The invention also provides a kit of parts comprising (b) a dual muscarinic antagonist-β2 adrenergic agonist of the invention together with instructions for simultaneous, concurrent, separate or sequential use in combination with (a) a corticosteroid, for the treatment of a human or animal patient suffering from or susceptible to a said respiratory disease.

Further provided is a package comprising (b) a dual muscarinic antagonist-β2 adrenergic agonist of the invention and (a) a corticosteroid for the simultaneous, concurrent, separate or sequential use in the treatment of a said respiratory disease.

Further provided is a combination, product, kit of parts or package as hereinabove described wherein such combination, product, kit of parts or package further comprises (c) another active compound selected from: (i) PDE IV inhibitors, (ii) leukotriene D4 antagonists, (iii) inhibitors of egfr-kinase, (iv) p38 kinase inhibitors, (iv) JAK inhibitors and (v) NK1 receptor agonists for simultaneous, separate or sequential use.

It is an embodiment of the present invention that the combination, product, kit of parts or package comprise (b) a dual muscarinic antagonist-β2 adrenergic agonist of the invention and (a) a corticosteroid, as the sole active compounds.

It is also an embodiment of the present invention the use of (b) a dual muscarinic antagonist-β2 adrenergic agonist of the invention and (a) a corticosteroid without any other active compound for the preparation of a medicament for simultaneous, concurrent, separate or sequential use in the treatment of a respiratory disease as defined above.

Examples of suitable corticosteroids to be used in the combinations of the invention are prednisolone, methylprednisolone, dexamethasone, dexamethasone acetate, dexamethasone cipecilate, naflocort, deflazacort, halopredone acetate, budesonide, beclomethasone dipropionate, hydrocortisone, triamcinolone acetonide, fluocinolone acetonide, fluocinonide, clocortolone pivalate, methylprednisolone aceponate, dexamethasone palmitoate, tipredane, hydrocortisone aceponate, prednicarbate, alclometasone dipropionate, halometasone, methylprednisolone suleptanate, mometasone, mometasone furoate, rimexolone, prednisolone famesylate, ciciesonide, butixocort propionate, (6alpha,11beta,16beta,17alpha)-6,9-Difluoro-11-hydroxy-16-methyl-3-oxo-17-(1-oxopropoxy)androsta-1,4-diene-17-carbothioic acid S-methyl ester (RS-85095), 9alpha-Chloro-6alpha-fluoro-11beta-hydroxy-16alpha-methyl-3-oxo-17alpha-propanoyloxy-androsta-1,4-diene-17beta-carboxylic acid methyl ester (CGP-13774), 16alpha,17alpha-[(R)-Butylidenedioxy]-6alpha,9alpha-difluoro-11beta-hydroxy-3-oxo-4-androstene-17beta-carbothioic acid S-(2-oxotetrahydrofuran-3-y) ester (GW-250495), deltacortisone, NO-Prednisolone, NO-Budesonide, etiprednol dicloacetate, QAE-397, (3beta,5alpha,7beta)-3,7-Dihydroxyandrostan-17-one (7beta-OH-EPIA), 16alpha,17alpha-[(R)-Butylidenedioxy]-6alpha,9alpha-difluoro-11beta-hydroxy-17beta-(methylsulfanyl)androst-4-en-3-one (RPR-106541), deprodone propionate, fluticasone, fluticasone propionate, fluticasone furoate, halobetasol propionate, loteprednol etabonate, betamethasone butyrate propionate, flunisolide, prednisone, dexamethasone sodium phosphate, triamcinolone, betamethasone 17-valerate, betamethasone, betamethasone dipropionate, 21-Chloro-11beta-hydroxy-17alpha-[2-(methylsulfanyl)acetoxy]-4-pregnene-3,20-dione, desisobutyrylciclesonide, hydrocortisone acetate, hydrocortisone sodium succinate, prednisolone sodium phosphate and hydrocortisone probutate, prednisolone sodium metasulfobenzoate and clobetasol propionate.

The preferred corticosteroids to be used in the combinations of the invention are prednisolone, methylprednisolone, dexamethasone, naflocort, deflazacort, halopredone acetate, budesonide, beclomethasone dipropionate, hydrocortisone, triamcinolone acetonide, fluocinolone acetonide, fluocinonide, clocortolone pivalate, methylprednisolone aceponate, dexamethasone palmitoate, tipredane, hydrocortisone aceponate, prednicarbate, alclometasone dipropionate, halometasone, methylprednisolone suleptanate, mometasone furoate, rimexolone, prednisolone famesylate, ciclesonide, deprodone propionate, fluticasone, fluticasone propionate, fluticasone furoate, halobetasol propionate, loteprednol etabonate, betamethasone butyrate propionate, flunisolide, prednisone, dexamethasone sodium phosphate, triamcinolone, betamethasone 17-valerate, betamethasone, hydrocortisone acetate, hydrocortisone sodium succinate, prednisolone sodium phosphate and hydrocortisone probutate.

Particularly preferred corticosteroids under the present invention are: budesonide, beclomethasone dipropionate, mometasone furoate, ciclesonide, triamcinolone, triamcinolone acetonide, triamcinolone hexaacetonide, fluticasone, fluticasone propionate and fluticasone furoate optionally in the form of their racemates, their enantiomers, their diastereomers and mixtures thereof, and optionally their pharmacologically-compatible acid addition salts. More preferred are budesonide, mometasone furoate, fluticasone, fluticasone propionate and fluticasone furoate, being the most preferred corticosteroids are mometasone, fluticasone propionate and fluticasone furoate.

Any reference to corticosteroids within the scope of the present invention includes a reference to salts or derivatives thereof which may be formed from the corticosteroids. Examples of possible salts or derivatives include: sodium salts, sulphobenzoates, phosphates, isonicotinates, acetates, propionates, dihydrogen phosphates, palmitates, pivaiates, famesylates, aceponates, suleptanates, prednicarbates, furoates or acetonides. In some cases the corticosteroids may also occur in the form of their hydrates.

A particularly preferred embodiment of the present invention is a combination of a trans-4-[{3-[5-({[(2R)-2-hydroxy-2-(8-hydroxy-2-oxo-1,2-dihydroquinolin-5-yl)ethyl]amino}methyl)-1H-1,2,3-benzotriazol-1-yl]propyl} (methyl)amino]cyclohexyl hydroxy(di-2-thienyl)acetate saccharinate with a corticosteroid. Preferred corticosteroids are selected from budesonide, beclomethasone dipropionate, mometasone furoate, ciclesonide, fluticasone, fluticasone propionate and fluticasone furoate, more preferably, mometasone furoate, fluticasone propionate and fluticasone furoate.

According to another embodiment of the invention the corticosteroid is budesonide.

According to another embodiment of the invention the corticosteroid is mometasone furoate.

According to another embodiment of the invention the corticosteroid is fluticasone.

According to another embodiment of the invention the corticosteroid is fluticasone propionate.

According to another embodiment of the invention the corticosteroid is fluticasone furoate In an alternative execution the invention consist in a kit of parts comprising a dual muscarinic antagonist-β2 adrenergic agonist of the invention together with instructions for simultaneous, concurrent, separate or sequential use in combination with a corticosteroid for the treatment of a respiratory disease, in particular for the treatment of asthma or COPD.

The present invention may also be executed in the form of a package comprising a dual muscarinic antagonist-β2 adrenergic agonist of the invention and a corticosteroid for the simultaneous, concurrent, separate or sequential use in the treatment of a respiratory disease, in particular for the treatment of asthma or COPD.

It is also an object of the present invention a dual muscarinic antagonist-β2 adrenergic agonist of the invention for simultaneous, concurrent, separate or sequential use in combination with a corticosteroid for the treatment of a respiratory disease, in particular for the treatment of asthma or COPD.

It is also an object of the present invention the use of a dual muscarinic antagonist-β2 adrenergic agonist of the invention for the preparation of a medicament, for simultaneous, concurrent, separate or sequential use in combination with a corticosteroid for the treatment of a respiratory disease, in particular for the treatment of asthma or COPD.

The invention is also directed to a method of treating a patient suffering a disease or condition for use in the treatment of a pathological condition or disease associated with both muscarinic receptor antagonist and β2 adrenergic receptor agonist activities, in particular for the treatment of respiratory diseases (such as, asthma, acute or chronic bronchitis, emphysema, chronic obstructive pulmonary disease (COPD), bronchial hyperreactivity or rhinitis), pre-labor, glaucoma, neurological disorders, cardiac disorders, inflammation and gastrointestinal disorders, more preferably respiratory disease, such as asthma or COPD, comprising administering to the patient an effective amount of a dual muscarinic antagonist-β2 adrenergic agonist of the invention and a corticosteroid.

Any reference to corticosteroids within the scope of the present invention includes a reference to salts or derivatives thereof which may be formed from the corticosteroids. Examples of possible salts or derivatives include: sodium salts, sulphobenzoates, phosphates, isonicotinates, acetates, propionates, dihydrogen phosphates, palmitates, pivaiates, famesylates, aceponates, suleptanates, prednicarbates, furoates or acetonides. In some cases the corticosteroids may also occur in the form of their hydrates.

More preferably the corticosteroid may be selected from the group comprising budesonide, beclomethasone, mometasone, ciclesonide and fluticasone optionally in the form of their racemates, their enantiomers, their diastereomers and mixtures thereof, and optionally their pharmacologically-compatible acid addition salts and more preferably, the corticosteroid is selected from mometasone, budesonide and fluticasone, being most preferably mometasone and fluticasone.

A preferred embodiment is the combination of trans-4-[{3-[5-({[(2R)-2-hydroxy-2-(8-hydroxy-2-oxo-1,2-dihydroquinolin-5-yl)ethyl]amino}methyl)-1H-1,2,3-benzotriazol-1-yl]propyl}(methyl)amino]cyclohexyl hydroxy(di-2-thienyl)acetate, or any pharmaceutically acceptable salt or solvate thereof with fluticasone propionate and combination of trans-4-[{3-[5-({[(2R)-2-hydroxy-2-(8-hydroxy-2-oxo-1,2-dihydroquinolin-5-yl)ethyl]amino}methyl)-1H-1,2,3-benzotriazol-1-yl]propyl}(methyl)amino]cyclohexyl hydroxy(di-2-thienyl)acetate, or any pharmaceutically acceptable salt or solvate thereof with fluticasone furoate and the combination of trans-4-[{3-[5-({[(2R)-2-hydroxy-2-(8-hydroxy-2-oxo-1,2-dihydroquinolin-5-yl)ethyl]amino}methyl)-1H-1,2,3-benzotriazol-1-yl]propyl}(methyl)amino]cyclohexyl hydroxy(di-2-thienyl)acetate, or any pharmaceutically acceptable salt or solvate thereof with budesonide and also a combination of trans-4-[{3-[5-({[(2R)-2-hydroxy-2-(8-hydroxy-2-oxo-1,2-dihydroquinolin-5-yl)ethyl]amino}methyl)-1H-1,2,3-benzotriazol-1-yl]propyl}(methyl)amino]cyclohexyl hydroxy(di-2-thienyl)acetate, or any pharmaceutically acceptable salt or solvate thereof with mometasone furoate.

The combinations of the invention can optionally comprise one or more additional active substances which are known to be useful in the treatment of respiratory disorders, such as PDE4 inhibitors, leukotriene D4 inhibitors, inhibitors of egfr-kinase, p38 kinase inhibitors, JAK inhibitors and/or NK1-receptor antagonists.

The invention thus provides a method of treating a disease or condition associated with dual muscarinic receptor and β2 adrenergic receptor activities (e.g. a respiratory disease, such as asthma or chronic obstructive pulmonary disease, pre-term labor, glaucoma, a neurological disorder, a cardiac disorder, inflammation, urological disorders such as urinary incontinence and gastrointestinal disorders such as irritable bowel syndrome or spastic colitis) in a mammal, comprising administering to the mammal, a therapeutically effective amount of a compound of formula (I) with one or more other therapeutic agents.

Examples of suitable PDE4 inhibitors to be used in the combinations of the invention are benafentrine dimaleate, etazolate, denbufylline, rolipram, cipamfylline, zardaverine, arofylline, filaminast, tipelukast, tofimilast, piclamilast, tolafentrine, mesopram, drotaverine hydrochloride, lirimilast, roflumilast, cilomilast, oglemilast, apremilast, tetomilast, filaminast, (R)-(+)-4-[2-(3-Cyclopentyloxy-4-methoxyphenyl)-2-phenylethyl]pyridine (CDP-840), N-(3,5-Dichloro-4-pyridinyl)-2-[1-(4-fluorobenzyl)-5-hydroxy-1H-indol-3-yl]-2-oxoacetamide (GSK-842470), 9-(2-Fluorobenzyl)-N6-methyl-2-(trifluoromethyl)adenine (NCS-613), N-(3,5-Dichloro-4-pyridinyl)-8-methoxyquinoline-5-carboxamide (D-4418), 3-[3-(Cyclopentyloxy)-4-methoxybenzyl]-6-(ethylamino)-8-isopropyl-3H-purine hydrochloride (V-11294A), 6-[3-(N,N-Dimethylcarbamoyl)phenylsulfonyl]-4-(3-methoxyphenylamino)-8-methylquinoline-3-carboxamide hydrochloride (GSK-256066), 4-[6,7-Diethoxy-2,3-bis(hydroxymethyl)naphthalen-1-yl]-1-(2-methoxyethyl)pyridin-2(1H)-one (T-440), (−)-trans-2-[3'-[3-(N-Cyclopropylcarbamoyl)-4-oxo-1,4-dihydro-1,8-naphthyridin-1-yl]-3-fluorobiphenyl-4-yl] cyclopropanecarboxylic acid (MK-0873), CDC-801, UK-500001, BLX-914, 2-carbomethoxy-4-cyano-4-(3-cyclopropylmethoxy-4-difluromethoxyphenyl)cyclohexan1-one, cis [4-cyano-4-(3-cyclopropylmethoxy-4-difluoromethoxyphenyl)cyclohexan-1-ol, CDC-801 and 5(S)-[3-(Cyclopentyloxy)-4-methoxyphenyl]-3(S)-(3-methylbenzyl)piperidin-2-one (IPL-455903).

Examples of suitable LTD4 antagonists to be used in the combinations of the invention are tomelukast, ibudilast, pobilukast, pranlukast hydrate, zafirlukast, ritolukast, verlukast, sulukast, cinalukast, iralukast sodium, montelukast sodium, 4-[4-[3-(4-Acetyl-3-hydroxy-2-propylphenoxy)propylsulfonyl]phenyl]-4-oxobutyric acid, [[5-[[3-(4-Acetyl-3-hydroxy-2-propylphenoxy)propyl]thio]-1,3,4-thiadiazol-2-yl]thio]acetic acid, 9-[(4-Acetyl-3-hydroxy-2-n-propylphenoxy)methyl]-3-(1H-tetrazol-5-yl)-4H-pyrido[1,2-a]pyrimidin-4-one, 5-[3-[2-(7-Chloroquinolin-2-yl)vinyl]phenyl]-8-(N,N-dimethylcarbamoyl)-4,6-dithiaoctanoic acid sodium salt; 3-[1-[3-[2-(7-Chloroquinolin-2-yl)vinyl]phenyl]-1-[3-(dimethylamino)-3-oxopropylsulfanyl]methylsulfanyl]propionic acid sodium salt, 6-(2-Cyclohexylethyl)-[1,3,4]thiadiazolo[3,2-a]-1,2,3-triazolo[4,5-d]pyrimidin-9(1H)-one, 4-[6-Acetyl-3-[3-(4-acetyl-3-hydroxy-2-propylphenylthio)propoxy]-2-propylphenoxy]butyric acid, (R)-3-Methoxy-4-[1-methyl-5-[N-(2-methyl-4,4,4-trifluorobutyl)carbamoyl]indol-3-ylmethyl]-N-(2-methylphenylsulfonyl)benzamide, (R)-3-[2-Methoxy-4-[N-(2-methylphenylsulfonyl)carbamoyl]benzyl]-1-methyl-N-(4,4,4-trifluoro-2-methylbutyl)indole-5-carboxamide and (+)-4(S)-(4-Carboxyphenylthio)-7-[4-(4-phenoxybutoxy)phenyl]-5(Z)-heptenoic acid.

Examples of suitable inhibitors of egfr-kinase to be used in the combinations of the invention are palifermin, cetuximab, gefitinib, repifermin, erlotinib hydrochloride, canertinib dihydrochloride, lapatinib, and N-[4-(3-Chloro-4-fluorophenylamino)-3-cyano-7-ethoxyquinolin-6-yl]-4-(dimethylamino)-2(E)-butenamide.

Examples of suitable p38 kinase inhibitors to be used in the combinations of the invention are chlormethiazole edisylate, doramapimod, 5-(2,6-Dichlorophenyl)-2-(2,4-difluorophenylsulfanyl)-6H-pyrimido[3,4-b]pyrazin-6-one, 4-Acetamido-N-(tert-butyl)benzamide, SCIO-469 (described in Clin Pharmacol. Ther. 2004, 75(2): Abst PII-7 and VX-702 described in Circulation 2003, 108(17, Suppl. 4): Abst 882.

Example of JAK inhibitors to be used in the combinations of the invention are Janus kinase (JAK) inhibitors, such as 3-[4(R)-Methyl-3(R)-[N-methyl-N-(7H-pyrrolo[2,3-d]pyrimidin-4-yl)amino]piperidin-1-yl]-3-oxopropanenitrile citrate (tofacitinib), ASP-015K, JTE-052, 3(R)-Cyclopentyl-3-[4-(7H-pyrrolo[2,3-d]pyrimidin-4-y)-1H-pyrazol-1-yl] propanenitrile phosphate (Ruxolitinib), 5-Chloro-N2-[1 (S)-(5-fluoropyrimidin-2-yl)ethyl]-N4-(5-methyl-1H-pyrazol-3-yl)pyrimidine-2,4-diamine (AZD-1480), 2-[1-(Ethylsulfonyl)-3-[4-(7H-pyrrolo[2,3-d]pyrimidin-4-yl)-1H-pyrazol-1-yl]azetidin-3-yl]acetonitrile (Baricitinib) and N-(Cyanomethyl)-4-[2-[4-(4-morpholinyl)phenylamino]-pyrimidin-4-yl]benzamide dihydrochloride (Momelotinib).

Examples of suitable NK1-receptor antagonists to be used in the combinations of the invention are nolpitantium besilate, dapitant, lanepitant, vofopitant hydrochloride, aprepitant, ezlopitant, N-[3-(2-Pentylphenyl)propionyl]-threonyl-N-methyl-2,3-dehydrotyrosyl-leucyl-D-phenylalanyl-allo-threonyl-asparaginyl-serine C-1.7-O-3.1 lactone, 1-Methylindol-3-ylcarbonyl-[4(R)-hydroxy]-L-prolyl-[3-(2-naphthyl)]-L-alanine N-benzyl-N-methylamide, (+)-(2S,3S)-3-[2-Methoxy-5-(trifluoromethoxy)benzylamino]-2-phenylpiperidine, (2R,4S)—N-[1-[3,5-Bis(trifluoromethyl)benzoyl]-2-(4-chlorobenzyl)piperidin-4-yl]quinoline-4-carboxamide, 3-[2(R)-[1(R)-[3,5-Bis(trifluoromethyl)phenyl]ethoxy]-3(S)-(4-fluorophenyl)morpholin-4-ylmethyl]-5-oxo-4,5-dihydro-1H-1,2,4-triazole-1-phosphinic acid bis(N-methyl-D-glucamine) salt; [3-[2(R)-[(R)-[3,5-bis(trifluoromethyl)phenyl]ethoxy]-3(S)-(4-fluorophenyl)-4-morpholinylmethyl]-2,5-dihydro-5-oxo-1H-1,2,4-triazol-1-yl]phosphonic acid 1-deoxy-1-(methylamino)-D-glucitol (1:2) salt, 1'-[2-[2(R)-(3,4-Dichlorophenyl)-4-(3,4,5-trimethoxybenzoyl)morpholin-2-yl]ethyl]spiro[benzo[c]thiophen-1 (3H)-4'-piperidine]2(S)-oxide hydrochloride and the compound CS-003 described in Eur Respir J 2003, 22(Suppl. 45): Abst P2664.

The combinations of the invention may be used in the treatment of any disorder which associated with both muscarinic receptors and β2 adrenergic receptors activities. Thus, the present application encompasses methods of treatment of these disorders, as well as the use of the combinations of the invention in the manufacture of a medicament for the treatment of these disorders.

Preferred examples of such disorders are those respiratory diseases, wherein the use of bronchodilating agents is expected to have a beneficial effect, for example asthma, acute or chronic bronchitis, emphysema, Chronic Obstructive Pulmonary Disease (COPD), bronchial hypperraeactivity or rhinitis, preferably asthma or Chronic Obstructive Pulmonary Disease (COPD).

The active compounds in the combinations of the invention may be administered by any suitable route, depending on the nature of the disorder to be treated, e.g. orally (as syrups, tablets, capsules, lozenges, controlled-release preparations, fast-dissolving preparations, lozenges, etc); topically (as creams, ointments, lotions, nasal sprays or aerosols, etc); by injection (subcutaneous, intradermic, intramuscular, intravenous, etc.) or by inhalation (as a dry powder, a solution, a dispersion, etc).

The active compounds in the combination, i.e. the dual muscarinic antagonist-β2 agonist of the invention, the corticosteroid and any other optional active compounds may be administered together in the same pharmaceutical composition or in different compositions intended for separate, simultaneous, concomitant or sequential administration by the same or a different route.

One execution of the present invention consists of a kit of parts comprising the dual muscarinic antagonist-β2 agonist of the invention together with instructions for simultaneous, concurrent, separate or sequential use in combination with a corticosteroid for the treatment of a respiratory disease as defined above.

Another execution of the present invention consists of a package comprising the dual muscarinic antagonist-β2 agonist of the invention and a corticosteroid for the simultaneous, concurrent, separate or sequential use in the treatment of a respiratory disease as defined above.

In a preferred embodiment of the invention the active compounds in the combination are administered by inhalation through a common delivery device, wherein they can be formulated in the same or in different pharmaceutical compositions.

In the most preferred embodiment the dual muscarinic antagonist-β2 agonist of the invention and the corticosteroid are both present in the same pharmaceutical composition and are administered by inhalation through a common delivery device.

Typically, the pharmaceutical compositions comprising the combination of the present invention and a pharmaceutically acceptable carrier are suitable for administration by inhalation and may further comprise a therapeutically effective amount of one or more other therapeutic agents, as defined herein. However, any other form of topical, parenteral or oral application is possible. The application of inhaled dosage forms embodies the preferred application form, especially in the therapy of diseases or disorders of the lung.

The pharmaceutical formulations may conveniently be presented in unit dosage form and may be prepared by any of the methods well known in the art of pharmacy. All methods include the step of bringing the active ingredient(s) into association with the carrier. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A syrup formulation will generally consist of a suspension or solution of the compound or salt in a liquid carrier for example, ethanol, peanut oil, olive oil, glycerine or water with flavouring or colouring agent.

Where the composition is in the form of a tablet, any pharmaceutical carrier routinely used for preparing solid formulations may be used. Examples of such carriers include magnesium stearate, talc, gelatine, acacia, stearic acid, starch, lactose and sucrose.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Where the composition is in the form of a capsule, any routine encapsulation is suitable, for example using the aforementioned carriers in a hard gelatine capsule. Where the composition is in the form of a soft gelatine capsule any pharmaceutical carrier routinely used for preparing dispersions or suspensions may be considered, for example aqueous gums, celluloses, silicates or oils, and are incorporated in a soft gelatine capsule.

Dry powder compositions for topical delivery to the lung by inhalation may, for example, be presented in capsules and cartridges of for example gelatine or blisters of for example laminated aluminium foil, for use in an inhaler or insufflator. Formulations generally contain a powder mix for inhalation of the compound of the invention and a suitable powder base (carrier substance) such as lactose or starch. Use of lactose is preferred. Alternatively, the active ingredient (s) may be presented without excipients.

The carrier for a pharmaceutical composition in the form of a dry powder is typically chosen from starch or a pharmaceutically acceptable sugar, such as lactose or glucose. Lactose is preferred.

Additional suitable carriers can be found in Remington: The Science and Practice of Pharmacy, 20th Edition, Lippincott Williams & Wilkins, Philadelphia, Pa., 2000.

The pharmaceutical compositions for inhalation are delivered with the help of inhalers, such as dry powder inhalers, aerosols or nebulisers. The inhaler is typically configured to deliver, upon actuation, a therapeutically effective amount of one or more other therapeutic agents, as defined herein.

Packaging of the compound of the invention in the inhaler may be suitable for unit dose or multi-dose delivery. In the case of multi-dose delivery, the compound of the invention can be pre-metered or metered in use. Dry powder inhalers are classified into three groups: (a) single dose, (b) multiple unit dose and (c) multi dose devices.

For inhalers of the first type (a), single doses have been weighed by the manufacturer into small containers, which are mostly hard gelatine capsules. A capsule has to be taken from a separate box or container and inserted into a receptacle area of the inhaler. Next, the capsule has to be opened or perforated with pins or cutting blades in order to allow part of the inspiratory air stream to pass through the capsule for powder entrainment or to discharge the powder from the capsule through these perforations by means of centrifugal force during inhalation. After inhalation, the emptied capsule has to be removed from the inhaler again. Mostly, disassembling of the inhaler is necessary for inserting and removing the capsule, which is an operation that can be difficult and burdensome for some patients. Other drawbacks related to the use of hard gelatine capsules for inhalation powders are (a) poor protection against moisture uptake from the ambient air, (b) problems with opening or perforation after the capsules have been exposed previously to extreme relative humidity, which causes fragmentation or indenture, and (c) possible inhalation of capsule fragments. Moreover, for a number of capsule inhalers, incomplete expulsion has been reported.

Some capsule inhalers have a magazine from which individual capsules can be transferred to a receiving chamber, in which perforation and emptying takes place, as described in WO 92/03175. Other capsule inhalers have revolving magazines with capsule chambers that can be brought in line with the air conduit for dose discharge (e. g. WO 91/02558 and GB 2242134). They comprise the type of multiple unit dose inhalers (b) together with blister inhalers, which have a limited number of unit doses in supply on a disk or on a strip.

Blister inhalers provide better moisture protection of the medicament than capsule inhalers. Access to the powder is obtained by perforating the cover as well as the blister foil, or by peeling off the cover foil. When a blister strip is used instead of a disk, the number of doses can be increased, but it is inconvenient for the patient to replace an empty strip. Therefore, such devices are often disposable with the incorporated dose system, including the technique used to transport the strip and open the blister pockets.

Multi-dose devices (c) do not contain pre-measured quantities of the medicament containing powder. They consist of a relatively large container and a dose measuring principle that has to be operated by the patient. The container bears multiple doses that are isolated individually from the bulk of powder by volumetric displacement. Various dose measuring principles exist, including rotatable membranes (e.g. EP0069715) or disks (e.g. GB 2041763; EP 0424790; DE 4239402 and EP 0674533), rotatable cylinders (e.g. EP 0166294; GB 2165159 and WO 92/09322) and rotatable frustums (e.g. WO 92/00771), all having cavities which have to be filled with powder from the container. Other multi dose devices have measuring plungers with a local or circumferential recess to displace a certain volume of powder from the container to a delivery chamber or an air conduit (e.g. EP 0505321, WO 92/04068 and WO 92/04928), or measuring slides such as the Novolizer SD2FL (ex. Sofotec), also known as Genuair®, are described in WO 97/00703, WO 03/000325 and WO2006/008027 and in Greguletz et al., Am. J. Respir. Crit. Care Med., 2009, 179: A4578; H. Chrystyn et al., Int. J. Clinical Practice, 66, 3, 309-317, 2012, and H. Magnussen et at. *Respiratory Medicine* (2009) 103, 1832-1837.

Reproducible dose measuring is one of the major concerns for multi dose devices.

The powder formulation has to exhibit good and stable flow properties, because filling of the dose measuring cups or cavities is mostly under the influence of the force of gravity. For reloaded single dose and multiple unit dose inhalers, the dose measuring accuracy and reproducibility can be guaranteed by the manufacturer. Multi dose inhalers on the other hand, can contain a much higher number of doses, whereas the number of handlings to prime a dose is generally lower.

Because the inspiratory air stream in multi-dose devices is often straight across the dose measuring cavity, and because the massive and rigid dose measuring systems of multi dose inhalers cannot be agitated by this inspiratory air stream, the powder mass is simply entrained from the cavity and little de-agglomeration is obtained during discharge.

Consequently, separate disintegration means are necessary. However in practice, they are not always part of the inhaler design. Because of the high number of doses in multi-dose devices, powder adhesion onto the inner walls of the air conduits and the de-agglomeration means must be minimized and/or regular cleaning of these parts must be possible, without affecting the residual doses in the device. Some multi dose inhalers have disposable drug containers that can be replaced after the prescribed number of doses has been taken (e.g. WO 97/000703). For such semi-permanent multi dose inhalers with disposable drug containers, the requirements to prevent drug accumulation are even stricter.

In another embodiment, the combination of the present invention can also be administered via single dose dry powder inhalers such as the devices described in WO 2005/113042 or in EP1270034. These devices are low resistance unit dosage form inhalers. The unit dosage form of the dry powder formulation are capsules typically made of gelatin or a synthetic polymer, preferably hydroxypropyl methyl cellulose (HPMC), also known as hypromellose. The hypromellose capsules are preferably packaged in a blister. The blister is preferably a peel foil blister that allows patients to remove capsules stored therein without damaging them and optimizes product stability.

Medicaments for administration by inhalation desirably have a controlled particle size. The optimum particle size for inhalation into the bronchial system is usually 1-10 µm, preferably 2-5 µm. Particles having a size above 20 µm are generally too large when inhaled to reach the small airways. To achieve these particle sizes, the particles of the active ingredients as produced may be size reduced by conventional means, for example, by micronisation or supercritical fluid techniques. The desired fraction may be separated out by air classification or sieving. Preferably, the particles will be crystalline.

Achieving a high dose reproducibility with micronised powders is difficult because of their poor flowability and extreme agglomeration tendency. To improve the efficiency of dry powder compositions, the particles should be large while in the inhaler, but small when discharged into the respiratory tract. Thus, an excipient, for example a mono-, di- or polysaccharide or sugar alcohol, such as lactose, mannitol or glucose is generally employed. The particle size of the excipient will usually be much greater than the inhaled medicament within the present invention. When the excipient is lactose it will typically be present as lactose particles, preferably crystalline alpha lactose monohydrate, e.g., having an average particle size range of 20-1000 µm, preferably in the range of 90-150 µm. The average particle size can be measured using standard techniques known to those skilled in the art.

The median particle size approximately corresponds to the average and is the diameter where 50 mass-% of the particles have a larger equivalent diameter, and the other 50 mass-% have a smaller equivalent diameter. Hence the average particle size is generally referred to in the art as equivalent d50. The distribution of particle size around may affect flow properties, bulk density, etc. Hence to characterize a particle size diameter, other equivalent diameters can be used in addition to d50, such as d10 and d90. d10 is the equivalent diameter where 10 mass-% of the particles have a smaller diameter (and hence the remaining 90% is coarser). d90 is the equivalent diameter where 90 mass-% of the particles have a smaller diameter. In one embodiment, the lactose particles for use in formulations of the invention have a d10 of 90-160 µm, a d50 of 170-270 µm, and d90 of 290-400 µm. The d10, d50 and d90 values can be measured using standard techniques known to those skilled in the art.

Suitable lactose materials for use in the present invention are commercially available, e.g., from DMV International (Respitose GR-001, Respitose SV-001, Respitose SV-003 or a mixture thereof), Meggle (Capsulac 60, Inhalac 70, Inhalac 120, Inhalac 230, Capsulac 60 INH, Sorbolac 400, or a mixture thereof), and Borculo Domo (Lactohale 100-200, Lactohale 200-300 and Lactohale 100-300, or a mixture thereof).

In another embodiment, the carrier used may be in the form of a mixture of different types of carrier having different particles sizes. For example, a mixture of a fine carrier and a coarse carrier may be present in the formulation, wherein the average particle size of the fine carrier is lower than the average particle size of the coarse carrier. Preferably the fine carrier may have an average particle size range of 1-50 µm, preferably 2-20 µm, more preferably, 5-15 µm. The coarse carrier may have an average particle size range of 20-1000 µm, preferably 50-500 µm, more preferably 90-400 µm, being most preferably, 150-300 µm. The content of the fine carrier with respect to the coarse carrier may vary from 1% to 10%, preferably, from 3% to 6%, e.g., 5%, by weight of the total coarse carrier.

In one embodiment lactose particles for use in formulations of the invention is a mixture of a coarse lactose having a d10 of 90-160 µm, a d50 of 170-270 µm, and d90 of 290-400 µm and a fine lactose having a d10 of 2-4 µm, a d50 of 7-10 µm, and d90 of 15-24 µm.

The ratio by weight between the lactose particles and the active ingredients will depend on the inhaler device used, but is typically, e.g., 10:1 to 50.000:1, for example 20:1 to 10.000:1, e.g., 40-5.000:1.

Apart from applications through dry powder inhalers the compositions of the invention can also be administered in nebulisers, metered dose inhalers and aerosols which operate via propellant gases or by means of so-called atomisers, via which solutions of pharmacologically-active substances can be sprayed under high pressure so that a mist of inhalable particles results. The advantage of these atomisers is that the use of propellant gases can be completely dispensed with. Such atomisers are described, for example, in PCT Patent Application No. WO 91/14468 and International Patent Application No. WO 97/12687, reference here being made to the contents thereof.

Spray compositions for topical delivery to the lung by inhalation may for example be formulated as aqueous solutions or suspensions or as aerosols delivered from pressurised packs, such as a metered dose inhaler, with the use of a suitable liquefied propellant. Aerosol compositions suitable for inhalation can be either a suspension or a solution and generally contain the active ingredient (s) and a suitable propellant such as a fluorocarbon or hydrogen-containing chlorofluorocarbon or mixtures thereof, particularly hydrofluoroalkanes, e. g. dichlorodifluoromethane, trichlorofluoromethane, dichlorotetra-fluoroethane, especially 1,1,1,2-tetrafluoroethane, 1,1,1,2,3,3,3-heptafluoro-n-propane or a mixture thereof. Carbon dioxide or other suitable gas may also be used as propellant. The aerosol composition may be excipient free or may optionally contain additional formulation excipients well known in the art such as surfactants e.g. oleic acid or lecithin and cosolvents e.g. ethanol. Pressurised formulations will generally be retained in a canister (e.g. an aluminium canister) dosed with a valve (e.g. a metering valve) and fitted into an actuator provided with a mouthpiece.

Pressurized aerosol compositions will generally be filled into canisters fitted with a valve, especially a metering valve. Canisters may optionally be coated with a plastics material e. g. a fluorocarbon polymer as described in WO96/32150. Canisters will be fitted into an actuator adapted for buccal delivery.

Typical compositions for nasal delivery include those mentioned above for inhalation and further include non-pressurized compositions in the form of a solution or suspension in an inert vehicle such as water optionally in combination with conventional excipients such as buffers, anti-microbials, tonicity modifying agents and viscosity modifying agents which may be administered by nasal pump.

Typical dermal and transdermal formulations comprise a conventional aqueous or non-aqueous vehicle, for example a cream, ointment, lotion or paste or are in the form of a medicated plaster, patch or membrane.

Preferably the composition is in unit dosage form, for example a tablet, capsule or metered aerosol dose, so that the patient may administer a single dose.

Each dosage unit contains suitably from 1 µg to 1000 µg of a dual muscarinic antagonist+β2 adrenergic agonist compound according to the invention or a pharmaceutical acceptable salt thereof and 10 µg to 1000 µg of a corticosteroid according to the invention.

The amount of each active which is required to achieve a therapeutic effect will, of course, vary with the particular active, the route of administration, the subject under treatment, and the particular disorder or disease being treated.

The active ingredients may be administered from 1 to 6 times a day, sufficient to exhibit the desired activity. Preferably, the active ingredients are administered once or twice a day.

The proportions in which (a) the corticosteroid and (b) the dual muscarinic antagonist-β2 adrenergic agonist may be used according to the invention are variable. Active substances (a) and (b) may possibly be present in the form of their pharmaceutically acceptable salts or solvates or hydrates. Depending on the choice of the compounds (a) and (b), the weight ratios, which may be used within the scope of the present invention, vary on the basis of the different molecular weights of the various salt forms.

The pharmaceutical combinations according to the invention may contain (a) the corticosteroid and (b) the dual muscarinic antagonist-β2 adrenergic agonist of the present invention generally in a ratio by weight (b):(a) ranging from 1:100 to 1000:1, preferably from 1:50 to 500:1.

It is contemplated that all active agents would be administered at the same time, or very close in time. Alternatively, one or two actives could be taken in the morning and the other (s) later in the day. Or in another scenario, one or two actives could be taken twice daily and the other (s) once daily, either at the same time as one of the twice-a-day dosing occurred, or separately. Preferably at least two, and more preferably all, of the actives would be taken together at the same time. Preferably, at least two, and more preferably all actives would be administered as an admixture.

The active substance compositions according to the invention are preferably administered in the form of compositions for inhalation delivered with the help of inhalers, especially dry powder inhalers, however, any other form or parenteral or oral application is possible. Here, the application of inhaled compositions embodies the preferred application form, especially in the therapy of obstructive lung diseases or for the treatment of asthma.

The following preparations forms are cited as formulation examples:

Example 1 Inhalable Powder

| Ingredient | Amount in mg |
| --- | --- |
| trans-4-[{3-[5-({[(2R)-2-hydroxy-2-(8-hydroxy-2-oxo-1,2-dihydroquinolin-5-yl)ethyl]amino}methyl)-1H-1,2,3-benzotriazol-1-yl]propyl}(methyl)amino]cyclohexyl hydroxy(di-2-thienyl)acetate saccharinate | 50 |
| Budesonide | 200 |
| Lactose | 4750 |

Example 2 Inhalable Powder

| Ingredient | Amount in mg |
| --- | --- |
| trans-4-[{3-[5-({[(2R)-2-hydroxy-2-(8-hydroxy-2-oxo-1,2-dihydroquinolin-5-yl)ethyl]amino}methyl)-1H-1,2,3-benzotriazol-1-yl]propyl}(methyl)amino]cyclohexyl hydroxy(di-2-thienyl)acetate saccharinate | 50 |
| Mometasone furoate | 200 |
| Lactose | 4750 |

Example 3 Inhalable Powder

| Ingredient | Amount in mg |
| --- | --- |
| trans-4-[{3-[5-({[(2R)-2-hydroxy-2-(8-hydroxy-2-oxo-1,2-dihydroquinolin-5-yl)ethyl]amino}methyl)-1H-1,2,3-benzotriazol-1-yl]propyl}(methyl)amino]cyclohexyl hydroxy(di-2-thienyl)acetate saccharinate | 50 |
| Fluticasone propionate | 150 |
| Lactose | 4800 |

Example 4 Inhalable Powder

| Ingredient | Amount in mg |
| --- | --- |
| trans-4-[{3-[5-({[(2R)-2-hydroxy-2-(8-hydroxy-2-oxo-1,2-dihydroquinolin-5-yl)ethyl]amino}methyl)-1H-1,2,3-benzotriazol-1-yl]propyl}(methyl)amino]cyclohexyl hydroxy(di-2-thienyl)acetate saccharinate | 50 |
| Fluticasone furoate | 150 |
| Lactose | 4800 |

Example 5 Aerosol

| Ingredient | % by weight |
| --- | --- |
| trans-4-[{3-[5-({[(2R)-2-hydroxy-2-(8-hydroxy-2-oxo-1,2-dihydroquinolin-5-yl)ethyl]amino}methyl)-1H-1,2,3-benzotriazol-1-yl]propyl}(methyl)amino]cyclohexyl hydroxy(di-2-thienyl)acetate saccharinate | 0.25 |
| Fluticasone propionate | 0.40 |
| Isopropyl myristate | 0.10 |
| TG 227 | ad 100 |

Example 8 Aerosol

| Ingredient | % by weight |
| --- | --- |
| trans-4-[{3-[5-({[(2R)-2-hydroxy-2-(8-hydroxy-2-oxo-1,2-dihydroquinolin-5-yl)ethyl]amino}methyl)-1H-1,2,3-benzotriazol-1-yl]propyl}(methyl)amino]cyclohexyl hydroxy(di-2-thienyl)acetate saccharinate | 0.25 |
| Mometasone furoate | 0.40 |
| Isopropyl myristate | 0.10 |
| TG 227 | ad 100 |

Pharmacological Activity

Surprisingly, an unexpectedly beneficial therapeutic effect can be observed in the treatment of inflammatory or obstructive diseases of the respiratory tract if a dual M3 muscarinic antagonist-β2 adrenergic agonist compound of the present invention is used with one or more corticosteroids.

In particular the combination of the MABA compound of the present invention (Cpd2) with a corticosteroid such as fluticasone or mometasone produces significantly more anti-inflammatory effects in inhibiting IL-8 secretion induced by LPS in peripheral blood neutrophils when compared with the corresponding corticosteroid alone.

Consequently, the combinations of the invention possess therapeutically advantageous properties, which make them particularly suitable for the treatment of respiratory diseases in all kind of patients.

Material and Methods

5 Healthy subjects were included for leukocyte experiments. Pulmonary function tests (forced spirometry) and arterial blood gas measurements were performed during the days prior to sample.

Neutrophils were isolated from peripheral blood of healthy volunteers according to standard procedures established in the laboratory (Milara J et al., *Respiration* 2012; 83, 147-158).

Isolated neutrophils were incubated with different drugs (MABA compound, mometasone or fluticasone) or vehicle for 30 minutes before incubation with LPS (1 mcg/mL) (Lipopolysaccharide, a representative stimulus as inflammatory mediator) for 6 hours in standard cell culture conditions (37° C. and 5% $CO_2$). Supernatant were collected to measure IL-8 (the inflammatory marker).

IL-8 (Interleukin-8) was determined by ELISA according to the standard procedure.

Data was presented as mean±SEM (see FIG. 1 and FIG. 2). Statistical analysis of results was carried out by analysis of variance (ANOVA) followed by Bonferroni test, by Student's t test, or by non-parametric tests as appropriate (GraphPad Software Inc, San Diego, Calif., USA). Significance was accepted when P<0.05.

Results

The results obtained are shown in Tables 1 and 2 and in FIGS. 1 and 2.

TABLE 1

Effects of Cpd 2 and its combination with mometasone in inhibiting IL-8 secretion induced by LPS in peripheral blood neutrophils from healthy subjects (5 volunteers run in triplicate)

| Compound | % inhibition of IL-8 secretion |
|---|---|
| Vehicle | — |
| Cpd 2 (0.01 nM) | 4.17 |
| Mometasone (0.01 nM) | 2.85 |
| Cpd 2 (0.01 nM) + Mometasone (0.01 nM) (calculated) | 7.02 |
| Cpd2 (0.01 nM) + Mometasone (0.01 nM) (measured) | 24.11[#] |

[#]$p < 0.005$ vs Cpd 2 and mometasone

As it can be clearly seen from Table 1 and FIG. 1, the combination of mometasone with Cpd2 (the MABA compound of the present invention) produces synergistic effects in inhibiting IL-8 secretion induced by LPS in peripheral blood neutrophils compared with the corresponding component alone.

When Cpd 2 is associated with mometasone, the inhibition is greater than the one obtained by mometasone alone or by Cpd2 alone. In addition the difference in inhibition is statistically significant (24.11% vs 2.85% when compared with mometasone and 24.11% vs 4.17%, when compared with Cpd2 alone). This inhibitory effect elicited by the association of the MABA compound of the present invention with mometasone is significantly higher when compared with the calculated additive effect of both compounds.

TABLE 2

Effects of Cpd 2 and its combination with fluticasone in inhibiting IL-8 secretion induced by LPS in peripheral blood neutrophils from healthy subjects (5 volunteers run in triplicate)

| Compound | % inhibition of anti-inflammatory effect |
|---|---|
| Vehicle | — |
| Cpd 2 (0.01 nM) | 4.17 |
| Fluticasone (0.1 nM) | 10.18 |
| Cpd 2 (0.01 nM) + Fluticasone (0.1 nM) (calculated) | 14.35 |
| Cpd2 (0.01 nM) + Fluticasone (0.1 nM) (measured) | 24.57*[#], |

*$p < 0.05$ vs Fluticasone,
[#]$p < 0.005$ vs Cpd2

As it can be clearly seen from Table 2 and FIG. 2, the combination of fluticasone with the MABA compound of the present invention produces synergistic effects in inhibiting IL-8 secretion induced by LPS in peripheral blood neutrophils when compared with the corresponding component alone.

When Cpd 2 is associated with fluticasone, the inhibition is greater than the one obtained by fluticasone alone or by Cpd2 alone. In addition the difference in inhibition is statistically significant (24.57% vs 10.18%, when compared with fluticasone and 24.57% vs 4.17%, when compared with Cpd 2 alone). This inhibitory effect elicited by the association of the MABA compound of the present invention with fluticasone is significantly higher when compared with the calculated additive effect of both compounds.

BRIEF DESCRIPTION OF FIGURES

FIG. 1 shows the effects of Cpd 2 and its combination with mometasone in inhibiting IL-8 secretion induced by LPS in peripheral blood neutrophils from healthy subjects.

FIG. 2 shows the effects of Cpd 2 and its combination with fluticasone in inhibiting IL-8 secretion induced by LPS in peripheral blood neutrophils from healthy subjects.

The invention claimed is:

1. A combination comprising (a) a corticosteroid chosen from budesonide, mometasone furoate, fluticasone propionate and fluticasone furoate and (b) a dual muscarinic antagonist-β2 adrenergic agonist compound, wherein the dual muscarinic antagonist-β2 adrenergic agonist compound is trans-4-[{3-[5-({[(2R)-2-hydroxy-2-(8-hydroxy-2-oxo-1,2-dihydroquinolin-5-yl)ethyl]amino}methyl)-1H-1,2,3-benzotriazol-1-yl]propyl}(methyl)amino]cyclohexyl hydroxy (di-2-thienyl)acetate saccharinate, wherein the combination is in a form for inhalation by a patient, and wherein the combination of the (a) corticosteroid and (b) dual muscarinic antagonist-β2 adrenergic agonist is in a ratio by weight of (b) to (a) in a range chosen from 1:100 to 1000:1.

2. The combination according to claim 1, wherein the corticosteroid is budesonide.

3. The combination according to claim 1, wherein the corticosteroid is mometasone furoate.

4. The combination according to claim 1, wherein the corticosteroid is fluticasone propionate.

5. The combination according to claim 1, wherein the corticosteroid is fluticasone furoate.

6. The combination according to claim 1, wherein the (a) a corticosteroid and (b) a dual muscarinic antagonist-β2 adrenergic agonist compound form part of a single pharmaceutical composition.

7. The combination according to claim 1, further comprising at least one additional compound chosen from PDE IV inhibitors, leukotriene D4 antagonists, inhibitors of egfr-kinase, p38 kinase inhibitors, JAK inhibitors, and NK1 receptor agonists.

8. A method for treating a patient suffering from a respiratory disease chosen from asthma or chronic obstructive pulmonary disease comprising administering to the patient a therapeutically effective amount of a combination comprising (a) a corticosteroid chosen from budesonide, mometasone furoate, fluticasone propionate and fluticasone furoate and (b) a dual muscarinic antagonist-β2 adrenergic agonist compound, wherein the dual muscarinic antagonist-β2 adrenergic agonist compound is trans-4-[{3-[5-({[(2R)-2-hydroxy-2-(8-hydroxy-2-oxo-1,2-dihydroquinolin-5-yl)ethyl]amino}methyl)-1H-1,2,3-benzotriazol-1-yl]propyl}(methyl)amino]cyclohexyl hydroxy(di-2-thienyl)acetate saccharinate, and wherein the combination is in a form of inhalation by a patient.

9. The method according to claim 8, wherein the combination comprises a combined preparation for simultaneous, concurrent, separate or sequential use.

10. The method according to claim 9, wherein the preparation further comprises at least one additional compound chosen from PDE IV inhibitors, leukotriene D4 antagonists, inhibitors of egfr-kinase, p38 kinase inhibitors, JAK inhibitors, or NK1 receptor agonists.

11. A kit of parts comprising the combination according to claim 1, together with instructions for simultaneous, concurrent, separate or sequential use for the treatment of a human or animal patient suffering from or susceptible to a respiratory disease susceptible to amelioration by 32 adrenergic receptor agonist and muscarinic receptor antagonist activities.

12. The kit according to claim 11, further comprising at least one additional compound chosen from PDE IV inhibitors, leukotriene D4 antagonists, inhibitors of egfr-kinase, p38 kinase inhibitors, JAK inhibitors, or NK1 receptor agonists.

13. A package comprising the combination according to claim 1, for the simultaneous, concurrent, separate or sequential use in the treatment of a respiratory disease susceptible to amelioration by 32 adrenergic receptor agonist and muscarinic receptor antagonist activities.

14. The package according to claim 13, comprising at least one additional compound chosen from PDE IV inhibitors, leukotriene D4 antagonists, inhibitors of egfr-kinase, p38 kinase inhibitors, JAK inhibitors, or NK1 receptor agonists.

15. The method according to claim 8, wherein the respiratory disease is asthma.

16. The method according to claim 8, wherein the respiratory disease is chronic obstructive pulmonary disease.

17. The combination according to claim 1, wherein the ratio by weight of (b) to (a) is in a range chosen from 1:50 to 500:1.

18. A combination comprising (a) a corticosteroid chosen from mometasone furoate, fluticasone propionate, and fluticasone furoate and (b) a dual muscarinic antagonist-β2 adrenergic agonist compound, wherein the dual muscarinic antagonist-β2 adrenergic agonist compound is trans-4-[{3-[5-({[(2R)-2-hydroxy-2-(8-hydroxy-2-oxo-1,2-dihydroquinolin-5-yl)ethyl]amino}methyl)-1H-1,2,3-benzotriazol-1-yl]propyl}(methyl)amino]cyclohexyl hydroxy(di-2-thienyl)acetate saccharinate, wherein the combination is in a form for inhalation by a patient, and wherein the combination of the (a) corticosteroid and (b) dual muscarinic antagonist-β2 adrenergic agonist is in a ratio by concentration of (b) to (a) in a range of 1:1 to 1:10.

* * * * *

UNITED STATES PATENT AND TRADEMARK OFFICE
CERTIFICATE OF CORRECTION

PATENT NO. : 10,456,390 B2
APPLICATION NO. : 14/906957
DATED : October 29, 2019
INVENTOR(S) : Monica Aparici Virgili et al.

Page 1 of 1

It is certified that error appears in the above-identified patent and that said Letters Patent is hereby corrected as shown below:

On the Title Page

Item (30), under "Foreign Application Priority Data," "13382305" should read --13382305.4--.

In the Claims

Claim 11, Column 21, Line 32, "by 32" should read --by $\beta 2$--.

Claim 13, Column 22, Line 7, "by 32" should read --by $\beta 2$--.

Signed and Sealed this
Fourth Day of February, 2020

Andrei Iancu
*Director of the United States Patent and Trademark Office*